United States Patent
Burke

(10) Patent No.: US 7,220,406 B2
(45) Date of Patent: May 22, 2007

(54) METHOD FOR PROMOTING BONE FORMATION

(75) Inventor: Steven K. Burke, Sudbury, MA (US)

(73) Assignee: Genzyme Corporation, Cqmbridge, MA (US)

(*) Notice: Subject to any disclaimer, the term of this patent is extended or adjusted under 35 U.S.C. 154(b) by 597 days.

(21) Appl. No.: 10/686,808

(22) Filed: Oct. 16, 2003

(65) Prior Publication Data

US 2004/0120922 A1 Jun. 24, 2004

Related U.S. Application Data

(60) Provisional application No. 60/443,937, filed on Jan. 30, 2003, provisional application No. 60/420,489, filed on Oct. 22, 2002.

(51) Int. Cl.
*A61Q 5/12* (2006.01)

(52) U.S. Cl. ............... 424/78.12; 424/78.08; 424/78.1; 424/78.11; 424/78.31

(58) Field of Classification Search ............... 424/78.1, 424/78.12, 78.08, 78.11, 78.31
See application file for complete search history.

(56) References Cited

U.S. PATENT DOCUMENTS

| | | | |
|---|---|---|---|
| 5,487,888 A | 1/1996 | Mandeville, III et al. | |
| 5,496,545 A | 3/1996 | Holmes-Farley et al. | |
| 5,607,669 A | 3/1997 | Mandeville, III et al. | |
| 5,618,530 A | 4/1997 | Mandeville, III et al. | |
| 5,624,963 A | 4/1997 | Mandeville, III et al. | |
| 5,667,775 A | 9/1997 | Holmes-Farley et al. | |
| 5,679,717 A | 10/1997 | Mandeville, III et al. | |
| 5,693,675 A | 12/1997 | Mandeville, III et al. | |
| 5,702,696 A | 12/1997 | Mandeville, III et al. | |
| 5,703,188 A | 12/1997 | Mandeville, III et al. | |
| 5,837,674 A * | 11/1998 | Kumagai et al. ............... | 514/7 |
| 5,900,475 A | 5/1999 | Mandeville, III et al. | |
| 5,925,379 A | 7/1999 | Mandeville, III et al. | |
| 6,083,495 A | 7/2000 | Holmes-Farley et al. | |
| 6,083,497 A | 7/2000 | Huval et al. | |
| 6,177,478 B1 | 1/2001 | Holmes-Farley et al. | |
| 6,203,785 B1 | 3/2001 | Holmes-Farley et al. | |
| 6,423,754 B1 | 7/2002 | Holmes-Farley et al. | |
| 6,458,889 B1 * | 10/2002 | Trollsas et al. ............ | 525/54.1 |
| 6,509,013 B1 | 1/2003 | Holmes-Farley et al. | |
| 6,556,407 B2 | 4/2003 | Brando et al. | |
| 6,566,407 B2 | 5/2003 | Holmes-Farley et al. | |
| 6,726,905 B1 | 4/2004 | Mandeville, III et al. | |
| 6,733,780 B1 | 5/2004 | Tyler et al. | |
| 2002/0051822 A1 | 5/2002 | Atherton et al. | |
| 2002/0159968 A1 | 10/2002 | Petersen et al. | |
| 2002/0168333 A1 | 11/2002 | Burke | |
| 2002/0182168 A1 | 12/2002 | Holmes-Farley et al. | |
| 2002/0187120 A1 | 12/2002 | Holmes-Farley et al. | |
| 2002/0187121 A1 | 12/2002 | Burke | |
| 2003/0039627 A1 | 2/2003 | Holmes-Farley et al. | |
| 2003/0049226 A1 | 3/2003 | Burke et al. | |
| 2003/0086898 A1 | 5/2003 | Holmes-Farley et al. | |
| 2003/0133902 A1 | 7/2003 | Holmes-Farley et al. | |
| 2003/0224501 A1 * | 12/2003 | Young et al. ............... | 435/226 |

FOREIGN PATENT DOCUMENTS

| | | |
|---|---|---|
| WO | WO 93/04373 | 3/1993 |
| WO | WO 98/42355 | 10/1998 |
| WO | WO 03/057225 A2 | 7/2003 |

OTHER PUBLICATIONS

Moe, S., et al., "Sevelamer HCL Improves Parathyroid Hormone (PTH) and Bone Function in Peritoneal Dialysis (PD) Patients with Probable Low Turnover Bone Disease," *American J. of Kidney Diseases*, 37(4): A25 (abstract only-Tenth Annual Clinical Nephrology Meeting Abstracts), (2001).

Raggi, P., et al., "Sevelamer Preserves and Calcium Reduces Trabecular Bone Mineral Density," *J. American Society of Nephrology*, 14: 502A (abstract only), (2003).

Katsumata, K., et al., "Sevelamer Hydrochloride Prevents Ectopic Calcification and Renal Osteodystrophy in Chronic Renal Failure Rats," *Kidney International*, 64: 441-450 (2003).

Slatopolsky, E.A., et al., "RenaGel®, a Nonabsorbed Calcium- and Aluminum-Free Phosphate Binder, Lowers Serum Phosphorus and Parathyroid Hormone," *Kidney International*, 55: 299-307 (1999).

Chertow, G.M., et al., "Sevelamer With and Without Calcium and Vitamin D: Observations From a Long-Term Open-Label Clinical Trial," *J. Of Renal Nutrition*, 10(3): 125-132 (2000).

Chertow, G.M., et al., "Hyperparathyroidisnm and Dialysis Vintage," *Clinical Nephrology*, 54(4): 295-300 (2000).

(Continued)

*Primary Examiner*—Michael G. Hartley
*Assistant Examiner*—Leah Schlientz

(57) ABSTRACT

Amine polymers, particularly aliphatic amine polymers, are useful in the treatment and prevention of bone disease and in methods for promoting bone formation. Sevelemer, polyallylamine crosslinked with epichlorohydrin, which is sold under the tradename Renagel®, is the preferred polymer used in the invention.

30 Claims, 5 Drawing Sheets

OTHER PUBLICATIONS

Malluche, H.H., and Mawad, H., "Management of Hyperphosphataemia of Chronic Kidney Disease: Lessons From the Past and Future Directions," *Nephrol. Dial. Transplant.*, 17: 1170-1175 (2002).

Cannata-Andia, J.B., and Rodriguez-Garcia, M., "Hyperphosphataemia as a Cardiovascular Risk Factor -How to Manage the Problem," *Nephrol. Dial. Transplant.*, 17(Suppl. 11): 16-19 (2002).

Nolan, C.R., and Qunibi, W.Y., "Calcium Salts in the Treatment of Hyperphosphatemia in Hemodialysis Patients," *Current Opinion in Nephrology and Hypertension*, 12: 373-379 (2003).

Čižman, B., "Hyperphosphataemia and Treatment With Sevelamer in Haemodialysis Patients," *Nephrol. Dial. Transplant.*, 18(Suppl. 5): v47-v49 (2003).

Coco, M., and Rush, H., "Increased Incidence of Hip Fractures in Dialysis Patients With Low Serum Parathyroid Hormone," *Am. J. Kidney Diseases*, 36(6): 1115-1121 (2000).

Taal, M.W., et al., "Risk Factors for Reduced Bone Density in Haemodialysis Patients," *Nephrol. Dial. Transplant.*, 14: 1922-1928 (1999).

Taal, M.W., et al., "Total Hip Bone Mass Predicts Survival in Chronic Hemodialysis Patients," *Kidney International*, 63: 1116-1120 (2003).

Braun, J., et al., "Electron Beam Computed Tomography in the Evaluation of Cardiac Calcifications in Chronic Dialysis Patients," *American J. Kidney Diseases*, 27(3): 394-401 (1996).

Cozzolino, M., et al., "Role of Calcium-Phosphate and Bone-Associated Proteins on Vascular Calcification in Renal Failure," *J. Am. Soc. Nephrol.*, 12: 2511-2516 (2001).

Loghman-Adham, M., "Phosphate Binders for Control of Phosphate Retention in Chronic Renal Failure," *Pediatr. Nephrol.*, 13: 701-708 (1999).

Elder, G., "Pathophysiology and Recent Advances in the Management of Renal Osteodystrophy," *J. Bone and Mineral Research*, 17(12): 2094-2105 (2002).

Bardin, T., "Musculoskeletal Manifestations of Chronic Renal Failure," *Curr. Opin. Rheumatol.*, 15: 48-54 (2003).

Albaaj, F., and Hutchison, A.J., "Hyperphosphataemia in Renal Failure (Causes, Consequences and Current Management)," *Drugs*, 63(6): 577-596 (2003).

Martin, C.J., and Reams, S.M., "The Renal Dietitians's Role in Managing Hyperphosphatemia and Secondary Hyperparathyroidism in Dialysis Patients: A National Survey," *J. Renal Nutrition*, 13(2): 133-136 (2003).

Fontaine, M.A., et al., "Fracture and Bone Mineral Density in Hemodialysis Patients," *Clinical Nephrol.*, 54(3): 218-226 (2000).

Kleinpeter, M.A., "Spectrum of Complications Related to Secondary Hyperparathyroidism in a Peritoneal Dialysis Patients," *Advances in Peritoneal Dialysis*, 16: 286-290 (2000).

Chertow, G.M., et al., "Poly(allylamine hydrochloride) (RenaGel®): a noncalcemic phosphate binder for the treatment of hyperphosphatemia in chronic renal failure," *Am. J. Kid. Dis.*, 29: 66-71 (1997).

Goldberg, D.I., et al., "Effect of RenaGel, an non-absorbed, calcium-and aluminum-free phosphate binder, on serum phosphorus, calcium, and intact parathyroid hormone in end-stage renal disease patients," *Nephrol. Dial. Transplant.*, 13: 2303-2310 (1998).

Chertow, G.M., et al., "A randomized trial of sevelamer hydrochloride (RenaGel®) with and without supplemental calcium. Strategies for the control of hyperphosphatemia in hemodialysis patients," *Clin. Nephrol.*, 51: 18-26 (1999).

Bleyer, A.J., et al., "A comparison of the calcium-free phosphate binder sevelamer hydrochloride with calcium acetate in the treatment of hyperphosphatemia in hemodialysis patients," *Am. J. Kid. Dis.*, 33: 694-701 (1999).

Chertow, G.M., et al., "Long-term effects of sevelamer hydrochloride on the calcium x phosphorus product and lipid profile of haemodialysis patients," *Nephol. Dial. Transplant.*, 14: 2907-2914 (1999).

Chertow, G.M., et al., "Sevelamer attenuates the progression of coronary and aortic calcification in hemodialysis patients," *Kidney Int.*, 62: 245-252 (2002).

Chertow, G.M., Burke, S.K., Lazarus, J.M., Stenzel, K.HL, Wombolt, D., Goldberg, D., Boventre, J.V., and Slatopolsky, E., "Poly(allylamine hydrochloride) (RenaGel®): a noncalcemic phosphate binder for the treatment of hyperphosphatemia in chronic renal failure", Am. J. Kid. Dis. 29: 66-71 (1997).

Goldberg, D.I., Dillon, M.S., Slatopolsky, E.A. Garrett, B., Gray, J.R., Marbury, T., Weinberg, M., Wombolt, D., and Burke, S.K., "Effect of RenaGel, a non-absorbed, calcium-and aluminum-free phosphate binder, on serum phosphorus, calcium, and intact parathyroid hormone in end-stage renal disease patients," Nephrol Dial Transplant 13: 2303-2310, 1998.

Chertow, G.M., Dillon, M., Burke, S.K., Steg, M., Bleyer, A.J. Garrett, B.N., Domoto, D.T., Wilkes, B.M., Wombolt, D.G., and Slatopolsky, E., "A randomized trial of sevelamer hydrochoride (RenaGel®) with and without supplemental calcium. Strategies for the control of hyperphosphatemia in hemodialysis patients," Clin Nephrol. 51: 18-26 (1999).

Bleyer, A.J., Burke, S.K., Dillon, M., Garrett, B., Kant, K.S., Lynch, D., Raman, S.N. Shoenfeld, P., Teitelbaum, I., Zieg, S., ans Slatopolsky, E., "A comparison of the clacium-free phosphate binder sevelamer hydrochloride with calcium acetate in the treatment of hyperphosphatemia in hemodialysis patients," Am.J. Kid Dis. 33: 694-701 (1999).

Slatopolsky, E., Burke, S.K., Dillon, M.A. and the Renagel Study Group, "RenaGel®, a nonabsorbed calcium and-aluminum-free phosphate binder, lowers serum phosphorus and parathyroid hormone," Kidney Int. 55: 299-307 (1999).

Chertow, G.M., Burke, S.K., Dillon, M.A., and Slatopolsky, E. for the Renagel Study Group, "Long-term effects of sevelamer hydrochloride on the calcium x phosphorus product and lipid profile of haemodialysis patients," Nephol Dial. Transplant. 14: 2907-2914 (1999).

Chertow, G.M., Burke, S.K., Raggi, P., for the Treat to Goal Working Group, "Sevelamer attenuates the progression of coronary and aortic calcification in hemodialysis patients," Kidney Int. 62: 245-252 (2002).

* cited by examiner

| | Renagel | | | | Calcium | | | | p-value** |
|---|---|---|---|---|---|---|---|---|---|
| | N | Mean ± SD | Median | p-value* | N | Mean ± SD | Median | p-value* | |
| Trabecular Bone | | | | | | | | | |
| Day 0 | 33 | 160.8 ± 48.6 | 152.8 | | 39 | 167.7 ± 67.3 | 168.1 | | 0.7474 |
| Month 24 | 33 | 167.9 ± 50.8 | 156.2 | | 39 | 157.8 ± 72.3 | 146.4 | | 0.2730 |
| Change: Day 0 to Month 24 | 33 | 7.1 ± 21.0 | 3.3 | 0.0563 | 39 | −10.0 ± 19.5 | −13.9 | 0.0016 | 0.0008 |
| Percent Change: Day 0 to Month 24 | 33 | 5.2 ± 13.9 | 2.0 | 0.0357 | 39 | −6.9 ± 13.0 | −6.1 | 0.0026 | 0.0006 |
| Cortical Bone | | | | | | | | | |
| Day 0 | 33 | 269.4 ± 54.2 | 259.1 | | 39 | 281.7 ± 81.1 | 260.1 | | 0.7560 |
| Month 24 | 33 | 272.9 ± 61.7 | 255.8 | | 39 | 274.3 ± 79.0 | 257.5 | | 0.7906 |
| Change: Day 0 to Month 24 | 33 | 3.5 ± 33.7 | 1.4 | 0.5432 | 39 | −7.4 ± 33.8 | −10.4 | 0.1100 | 0.2097 |
| Percent Change: Day 0 to Month 24 | 33 | 1.6 ± 13.3 | 0.6 | 0.9096 | 39 | −1.9 ± 12.2 | −4.2 | 0.2423 | 0.3659 |

* Wilcoxon signed rank test, within group p-value; ** Wilcoxon rank sum test, between group p-value

FIG. 1

METHOD FOR PROMOTING BONE FORMATION

RELATED APPLICATIONS

This application claims the benefit of U.S. Provisional Application No. 60/420,489, filed Oct. 22, 2002, and U.S. Provisional Application No. 60/443,937, filed Jan. 30, 2003. The entire teachings of the above applications are incorporated herein by reference.

BACKGROUND OF THE INVENTION

Osteoporosis is a progressive condition in which bones gradually lose their strength and density. An estimated 1 million older Americans suffer broken bones (typically wrist, spinal vertebrae and hips) because of osteoporosis. Women typically account for the vast majority of injuries caused by osteoporosis.

Normally, bone is continuously removed by osteoclasts and is replaced with new bone that is produced by osteoblasts. Bone loss results when the balance of the constructive and destructive processes is tipped from equilibrium toward a loss of calcium and other bone components. Osteoporosis is typically caused by either environmental or genetic factors. Environmental factors include aging and endocrine disease (i.e., hyperthyroidism, hypogonadism, Cushing's Syndrome). Genetic factors include abnormal estrogen receptor gene, osteogenesis imperfecta tarda, and homocysteinuria.

One typical treatment for osteoporosis is hormone replacement therapy, however, the efficacy of such treatment is in doubt (Hulley, S., et al. J. Am. Med. Assoc. 280: 605–613 (1998)). Another treatment involves the use of bisphosphonates (e.g., alendronate, risedronate), raloxifene, and/or nasal calcitonin. All of the aforementioned antiresorptive agents currently approved for the treatment decrease bone resorption but do not induce new bone formation. Studies have shown that antiresorption agents may in fact prevent new bone formation and may contribute to increased fractures in patients who have been taking these agents from prolonged periods (Goodman R. L., New Engl. J. Med. 344(22):1720–1721 (2001); Mashiba, T., et al., Bone 28(5):424–31 (2001)). In addition, bisphosphonates can cause side effects involving the gastrointestinal tract.

Because osteoporosis is a common disease of aging and because the elderly population in the United States continues to grow, there is a clear need for new treatments for osteoporosis. Additionally, new treatments that could promote the formation of bone and that could prophylactically treat bone disorders are needed. Such new treatments should have minimal side effects, particularly systemic side effects.

SUMMARY OF THE INVENTION

Amine polymers are useful in promoting bone growth and/or preventing bone loss. It has been found that patients being treated with a cross-linked polyallylamine, sevelamer, experience increased levels of bone-specific alkaline phosphatase (BSAP) and osteocalcin, which indicate increased osteoblast function and enhanced bone formation (Example 1). The trabecular and cortical bone density in patients being treated with sevelamer has also been studied. In one trial, there was a significant increase in the trabecular bone density of these patients, while there was a non-significant increase in cortical bone density (Example 1). Surprisingly, patients treated with calcium instead of an amine polymer experienced a decrease in bone density over the same time period.

The invention relates to a method for treating osteoporosis using at least one amine polymer.

The invention further relates to a method for promoting bone formation in a mammal in need thereof using at least one amine polymer.

The invention also relates to a method for prophylactic treatment of a mammal that has a risk factor for bone loss using at least one amine polymer.

The present invention also includes the use of polymers disclosed herein in the manufacture of a medicament for the treatment of one of the conditions disclosed herein. For example, the invention includes the use of an amine polymer (e.g., a polyallylamine such as sevelamer) in the manufacture of a medicament for promoting bone formation or preventing bone loss.

In one embodiment of the invention, the mammal or patient being treated by one of the above methods is not suffering from hyperphosphatemia. In another embodiment, the mammal or patient is not suffering from hyperparathyroidism, hyperphosphatemia or osteitis fibrosa.

The methods disclosed by the present invention are capable of enhancing or at least preserving bone density in patients. The polymers disclosed herein are not associated with the calcification of non-bone tissues, particularly blood vessels. In addition, the polymers of the invention are typically non-absorbable and do not cause systemic side effects. Other features and advantages will be apparent from the following description of the preferred embodiments thereof and from the claims.

BRIEF DESCRIPTION OF THE DRAWING

FIG. 1 shows the results related to trabecular and cortical bone density for extension study patients in Example 1.

DETAILED DESCRIPTION OF THE INVENTION

Figure 2:
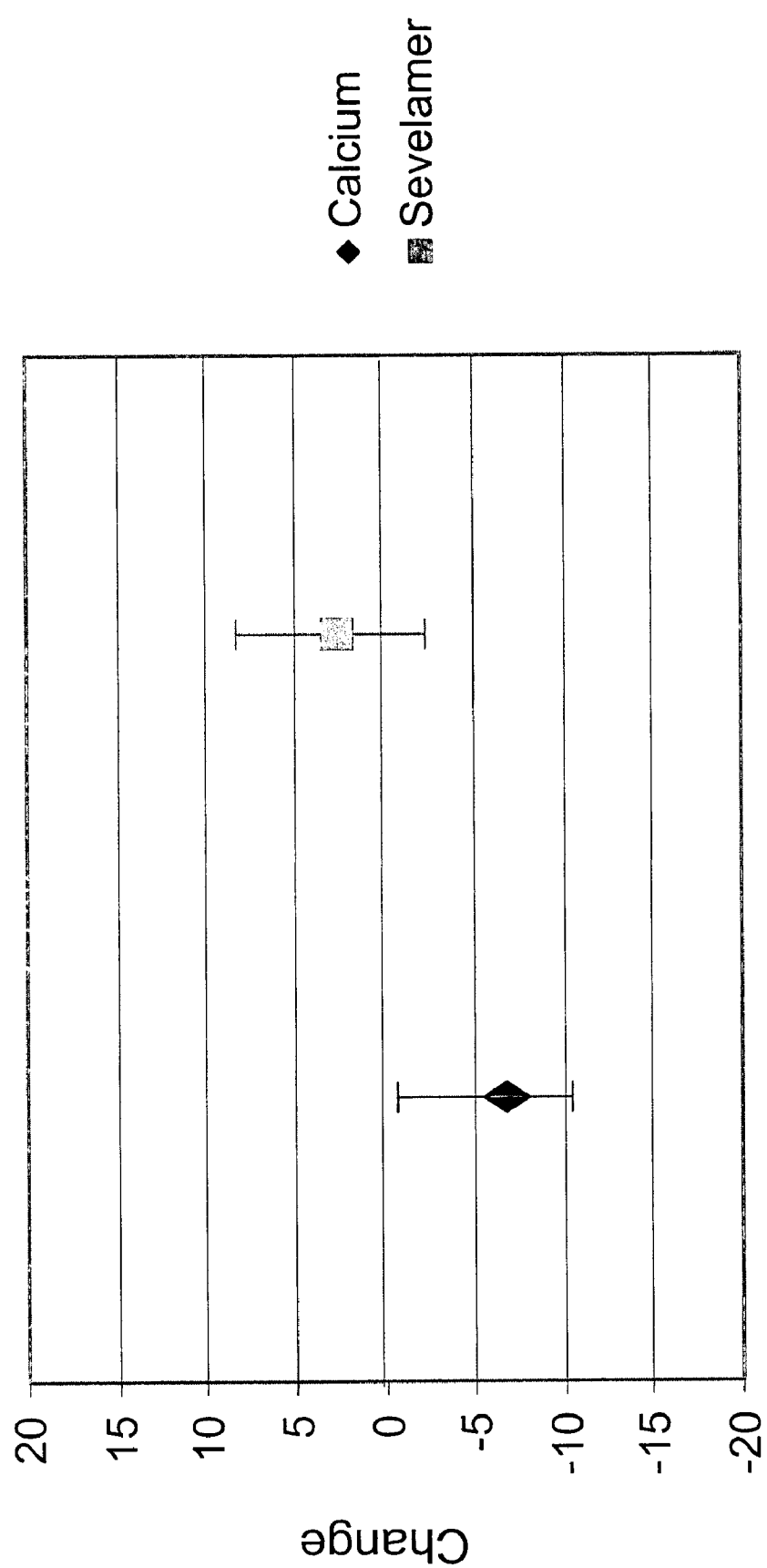
FIG. 2 shows the mean change in trabecular bone density over the one year period analyzed in Example 2. The bars indicate the 95% confidence interval.

Amine polymers are characterized by a repeat unit that includes at least one amino group. Amino groups can be part of the polymer backbone (e.g., polyethyleneimine), pendant from the polymer backbone (e.g., polyallylamine), or both types of amino groups can exist within the same repeat unit and/or polymer. Amine polymers include aliphatic amine polymers and aromatic amine polymers.

An aliphatic amine polymer used in the invention is a polymer which is manufactured by polymerizing an aliphatic amine monomer. Preferably these polymers are characterized by one or more monomeric units of Formula I,

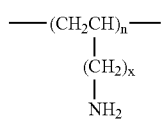
(I)

and salts thereof, where n is a positive integer and x is 0 or an integer between 1 and about 4, preferably 1. Preferably, the polymer is crosslinked by means of a multifunctional cross-linking agent. A particularly preferred polymer is an epichlorohydrin cross-linked polyallylamine, such as sevelamer.

Other examples of aliphatic amine polymers include polymers characterized by one or more repeat units set forth below:

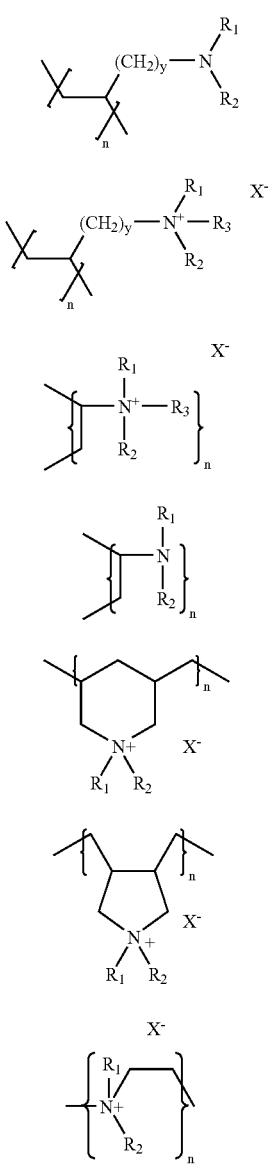

(II)
(III)
(IV)
(V)
(VI)
(VII)
(VIII)

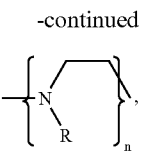

(IX)

or a salt or copolymer thereof, where n is a positive integer, y is an integer of one or more (e.g., between about one and about 10, preferably between one and four, more preferably one) and each R, $R_1$, $R_2$, and $R_3$, independently, is H or a substituted or unsubstituted alkyl group (e.g., having between 1 and 25 or between 1 and 5 carbon atoms, inclusive), alkylamino (e.g., having between 1 and 5 carbons atoms, inclusive, such as ethylamino or poly(ethylamino)) or aryl (e.g., phenyl) group, and each $X^-$ is an exchangeable negatively charged counterion.

In one preferred polymer used in the invention, at least one of R, $R_1$, $R_2$, or $R_3$ is a hydrogen atom. In a more preferred embodiment, each of these groups are hydrogen. In one embodiment, R, $R_1$, $R_2$, and $R_3$ are —H and the polymer comprises repeat units characterized by Structural Formulas (II), (III), (IV), (V), (VI), (VII), (VIII) and/or (IX).

As an alkyl, alkylamino or aryl group, R, $R_1$, $R_2$, and $R_3$ can carry one or more substituents. Suitable substituents include cationic groups, e.g., quaternary ammonium groups, or amine groups, e.g., primary, secondary or tertiary alkyl or aryl amines. Examples of other suitable substituents include hydroxy, alkoxy, carboxamide, sulfonamide, halogen, alkyl, aryl, hydrazine, guanidine, urea, poly(alkyleneimine) such as poly(ethylenimine), and carboxylic acid esters.

One particular type of aliphatic amine polymer used in the invention is a crosslinked polyalkyleneimine. A preferred polymer of this type is colestipol.

Aromatic amine polymers contain an aromatic moiety in one or more of the repeat units that contain an amino group. An example of an aromatic amine polymer is poly(aminostyrene).

Another type of aromatic amine polymer used in the invention is based on a heteroaryl monomer unit, such as a crosslinked alkylimidazole (e.g., a 2-alkylimidazole). Crosslinking agents are described below. A preferred polymer of this type is 2-methylimidazole crosslinked with epichlorohydrin, which is also known as colebine or MCI-196. Other polymers of this type include crosslinked vinylimidazole polymers and crosslinked vinylmethylimidazole polymers.

Many of the polymers listed above are also referred to as bile acid sequestrants.

Amine polymers used in the invention are optionally protonated, and typically include polymers in which significantly less than 40%, less than 30%, less than 20% or less than 10% of the amine groups are protonated.

An amine polymer can be a homopolymer or a copolymer of one or more amine-containing monomers or a copolymer of one or more amine-containing monomers in combination with one or more non-amine containing monomers. Copolymers that include one or more amine repeat units (e.g., repeat units represented by the Structural Formula (I)) preferably contain comonomers that are inert and non-toxic. Examples of suitable non-amine-containing monomers include vinyl alcohol, acrylic acid, acrylamide, and vinylformamide.

Preferably, an amine polymer (e.g., an aliphatic amine polymer) is a homopolymer, such as a homopolyallylamine, homopolyvinylamine, homopolydiallylamine or polyethyleneimine. The word "amine," as used herein, includes primary, secondary and tertiary amines, as well as ammonium groups such as trialkylammonium.

The preferred polymers employed in the invention comprise water-insoluble, non-absorbable, optionally cross-linked polyamines. Preferred polymers are aliphatic. Examples of preferred polymers include polyethyleneimine, polyallylamine, polyvinylamine and polydiallylamine polymers. The polymers can be homopolymers or copolymers and can be substituted or unsubstituted. These and other polymers which can be used in the claimed invention have been reported in U.S. Pat. Nos. 5,487,888, 5,496,545, 5,607,669, 5,618,530, 5,624,963, 5,667,775, 5,679,717, 5,703,188, 5,702,696, 5,693,675, 5,900,475, 5,925,379, 6,083,497, 6,177,478, 6,083,495, 6,203,785, 6,423,754, 6,509,013 and 6,556,407, and U.S. Published Applications 2002/0159968 A1, 2003/0086898 A1 and 2003/0133902 A1, the contents of which are hereby incorporated herein by reference in their entireties. Polymers suitable for use in the invention are also disclosed in co-pending U.S. application Ser. Nos. 08/823,699 (now abandoned); 08/835,857 (now abandoned); 08/470,940 (now abandoned); 08/927,247 (now abandoned); 08/964,498, 09/691,429 and 10/125,684, the contents of which are incorporated herein by reference in their entireties.

Preferably, the polymer is rendered water-insoluble by cross-linking. The cross-linking agent can be characterized by functional groups which react with the amino group of the monomer. Alternatively, the cross-linking group can be characterized by two or more vinyl groups which undergo free radical polymerization with the amine monomer. The degree of polymerization in cross-linked polymers (i.e., the value of "n") cannot generally be determined.

Examples of suitable multifunctional cross-linking agents include diacrylates and dimethylacrylates (e.g. ethylene glycol diacrylate, propylene glycol diacrylate, butylene glycol diacrylate, ethylene glycol dimethacrylate, propylene glycol dimethacrylate, butylene glycol dimethacrylate, polyethyleneglycol dimethacrylate and polyethyleneglycol diacrylate), methylene bisacrylamide, methylene bismethacrylamide, ethylene bisacrylamide, ethylene bismethacrylamide, ethylidene bisacrylamide, divinylbenzene, bisphenol A, dimethacrylate and bisphenol A diacrylate. The cross-linking agent can also include 1,3-dichloropropane, 1,3-dibromopropane, 1,2-dichloropropane, 1,2-dibromopropane, acryloyl chloride, epichlorohydrin, butanediol diglycidyl ether, ethanediol diglycidyl ether, dimethyl succinate, succinyl dichloride, the diglycidal ether of bisphenol A, pyromellitic dianhydride, toluene diisocyanate, ethylene diamine or dimethyl succinate.

A preferred cross-linking agent is epichlorohydrin because of its high availability and low cost. Epichlorohydrin is also advantageous because of its low molecular weight and hydrophilic nature, increasing the water-swellability and gel properties of the polyamine.

The level of cross-linking makes the polymers insoluble and substantially resistant to absorption and degradation, thereby limiting the activity of the polymer to the gastrointestinal tract, and reducing potential side-effects in the patient. The compositions thus tend to be non-systemic in activity. Typically, the cross-linking agent is present in an amount from about 0.5–35% or about 0.5–25% (such as from about 2.5–20% or about 1–10%) by weight, based upon total weight of monomer plus cross-linking agent.

The polymers can also be further derivatized; examples include alkylated amine polymers, as described, for example, in U.S. Pat. Nos. 5,679,717, 5,607,669 and 5,618,530, the teachings of which are incorporated herein by reference in their entireties. Preferred alkylating agents include hydrophobic groups (such as aliphatic hydrophobic groups) and/or quaternary ammonium- or amine-substituted alkyl groups.

Non-cross-linked and cross-linked polyallylamine and polyvinylamine are generally known in the art and are commercially available. Methods for the manufacture of polyallylamine and polyvinylamine, and cross-linked derivatives thereof, are described in the above U.S. patents. Patents by Harada, et al. (U.S. Pat. Nos. 4,605,701 and 4,528,347), which are incorporated herein by reference in their entireties, also describe methods of manufacturing polyallylamine and cross-linked polyallylamine. A patent by Stutts, et al. (U.S. Pat. No. 6,180,754) describes an additional method of manufacturing cross-linked polyallylamine.

In other embodiments, the polymer can be a homopolymer or copolymer of polybutenylamine, polylysine, or polyarginine. Alternatively, the polymer can be an aromatic polymer, such as an amine or ammonium-substituted polystyrene, (e.g., cholestyramine).

The molecular weight of polymers of the invention is not believed to be critical, provided that the molecular weight is large enough so that the polymer is non-absorbable by the gastrointestinal tract. Typically, the molecular weight is at least 1,000. For example, the molecular weight can be from about 1,000 to about 5 million, about 1,000 to about 3 million, about 1,000 to about 2 million or about 1,000 to about 1 million.

As described above, the polymer can be administered in the form of a salt. By "salt" it is meant that the nitrogen group in the repeat unit is protonated to create a positively charged nitrogen atom associated with a negatively charged counterion.

The anionic counterions can be selected to minimize adverse effects on the patient, as is more particularly described below. Examples of suitable counterions include organic ions, inorganic ions, or a combination thereof, such as halides ($Cl^-$ and $Br^-$), $CH_3OSO_3^-$, $HSO_4^-$, $SO_4^{2-}$, $HCO_3^-$, $CO_3^{2-}$, nitrate, hydroxide, persulfate, sulfite, acetate, lactate, succinate, propionate, oxalate, butyrate, ascorbate, citrate, dihydrogen citrate, tartrate, taurocholate, glycocholate, cholate, hydrogen citrate, maleate, benzoate, folate, an amino acid derivative, a nucleotide, a lipid, or a phospholipid. Preferred ions are chloride, carbonate and bicarbonate. The counterions can be the same as, or different from, each other. For example, the polymer can contain two different types of counterions.

A preferred polymer for use in the invention is polyallylamine which is a polymer having repeat units from polymerized allyl amine monomers. The amine group of an allyl monomer can be unsubstituted or substituted with, for example, one or two $C_1$–$C_{10}$ straight chain or branched alkyl groups. The alkyl group(s) is optionally substituted with one or more hydroxyl, amine, halo, phenyl, amide or nitrile groups. Preferably, the polyallylamine polymers of the present invention comprise repeat units represented by Structural Formula (X) or are crosslinked homopolymers thereof:

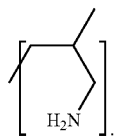

(X)

A polyallylamine can be a copolymer comprising repeat units from two or more different polymerized allyl monomers or with repeat units from one or more polymerized allyl monomers and repeat units from one or more polymerized non-allyl monomers. Examples of suitable non-allyl monomers include acrylamide monomers, acrylate monomer, maleic acid, malimide monomers, vinyl acylate monomers and alkyl substituted olefines. Preferably, however, the polyallylamines used in the present invention comprise repeat units solely from polymerized allyl amine monomer. More preferably, the polyallylamine polymers used in the present invention are homopolymers. Even more preferably, the polyallylamine polymers used in the present invention are homopolymers of repeat units represented by Structural Formula (X) or crosslinked homopolymers thereof.

Although a polyallylamine can be uncrosslinked, it is preferably crosslinked. Suitable crosslinking agents include epichlorohydrin, 1,4-butanedioldiglycidyl ether, 1,2-ethanedioldiglycidyl ether, 1,3-dichloropropane, 1,2-dichloroethane, 1,3-dibromopropane, 1,2-dibromoethane, succinyl dichloride, dimethylsuccinate, toluene diisocyanate, acryloyl chloride, and pyromellitic dianhydride. Epichlorohydrin is a preferred crosslinking agent, which forms 2-hydroxypropyl crosslinking groups. Typically, between about 9% and about 30% of the allylic nitrogen atoms are bonded to a crosslinking group, preferably between 15% and about 21%.

Polyallylamines can be protonated with organic or inorganic acids comprising physiologically acceptable anions. The anions can be partially or completely replaced with other physiologically acceptable anions by various means, including by passing the polymer over an anion exchange resin prior to crosslinking. A polyallyamine polymer can comprise more than one type of anion. Examples of suitable anions include halides ($Cl^-$ and $Br^-$), $CH_3OSO_3^-$, $HSO_4^-$, $SO_4^{2-}$, $HCO_3^-$, $CO_3^{2-}$, nitrate, hydroxide, persulfate, sulfite, acetate, lactate, succinate, propionate, oxalate, butyrate, ascorbate, citrate, dihydrogen citrate, tartrate, taurocholate, glycocholate, cholate, hydrogen citrate, maleate, benzoate, folate, an amino acid derivative, a nucleotide, a lipid, or a phospholipid. Chloride, carbonate and bicarbonate are preferred anions. The counteranions can be the same as or different from each other. For example, the polymer can contain two or more different types of couteranions.

Further preferred polyallylamine polymers used in the invention are those in which significantly less than 40%, such as less than 30%, particularly less than 20%, and more particularly less than 10%, of the amine groups are protonated.

In a preferred embodiment, the polyallylamine polymer is crosslinked with epichlorohydrin and between about 9% to about 30% (preferably about 15% to about 21%) of the allylic nitrogen atoms are bonded to a crosslinking group and the anion is chloride. More preferably, the polyallylamine polymer is a homopolymer. Even more preferably, the polyallylamine polymer is a homopolymer comprising repeat units represented by Structural Formula (X).

In a particularly preferred embodiment, the polyallylamine polymer used in the present invention is homopolyallyamine crosslinked with about 9.0–9.8% epichlorohydrin, preferably 9.3–9.5%, and is the active chemical component of the drug known as sevelamer HCl, sold under the tradename RENAGEL. Typically, the amount of epichlorohydrin is measured as a percentage of the combined weight of polymer and crosslinking agent. In another preferred embodiment, the polyallylamine polymer is sevelamer carbonate or sevelamer bicarbonate.

The polymer can be administered alone or in a pharmaceutical composition comprising the polymer, a pharmaceutically acceptable carrier or diluent, and optionally, one or more additional drugs. The polymers are preferably administered orally and even more preferably administered orally with a meal. Suitable carriers and diluents will be immediately apparent to persons skilled in the art. These carrier and diluent materials, either inorganic or organic in nature, include, for example, silicon oxide, stearic acid, gelatin, albumin, lactose, starch, magnesium stearate preservatives (stabilizers), melting agents, emulsifying agents, salts and buffers. The therapeutically effective amount can be administered in a series of doses separated by appropriate time intervals such as minutes or hours.

One form for oral delivery of a polymer of the invention is a direct compression tablet formulation as described in WO 01/28527 and U.S. Publication No. 2002/0054903 A1, the contents of which are incorporated herein by reference. The tablet core comprises at least about 95% by weight of an aliphatic amine polymer. A preferred aliphatic amine polymer is a cross-linked polyallylamine. The aliphatic amine polymer is preferably hydrated, typically from about 5% water by weight or greater (e.g., from about 5% water to about 10% water).

The tablet can further comprise one or more excipients, such as hardeners, glidants and lubricants, which are well known in the art. Suitable excipients include colloidal silicon dioxide, stearic acid, magnesium silicate, calcium silicate, sucrose, calcium stearate, glyceryl behenate, magnesium stearate, talc, zinc stearate and sodium stearylfumarate. The excipients can represent from 0 to about 5% of the tablet core by weight.

One preferred dosage form is a sevelamer hydrochloride tablet, which contains 400 or 800 mg of the active agent on an anhydrous basis. Sevelamer hydrochloride can also be administered as a capsule, preferably with 403 mg of active agent on an anhydrous basis. Excipients typically contained in a tablet include hydroxypropyl methylcellulose, diaceylated monoglyceride, colloidal silicon dioxide and stearic acid. Excipients typically contained in a capsule include colloidal silicon dioxide and stearic acid. Capsule exteriors typically contain titanium dioxide and indigo carmine ink.

A therapeutically effective amount is defined herein as a sufficient amount of an amine polymer to treat (including prophylactically treat) the conditions disclosed herein. Typically, the therapeutically effective daily dosages of aliphatic amine polymers range from 1 mg to 5 g. More typically, about 400 mg to about 2.5 g of an aliphatic amine polymer is administered daily. One particular dose is about 800 mg to about 1600 mg of an amine polymer (e.g., 1 to 4 sevelamer capsules or tablets, as described above, daily).

Examples of diseases and disorders that can be treated by the methods of the present invention include osteoporosis, Paget's disease, osteoarthritis, rheumatoid arthritis, achondroplasia, osteochondritis, hyperparathyroidism, osteogenesis imperfecta, congenital hypophosphatasia, fibromatous lesions, fibrous displasia, multiple myeloma, abnormal bone turnover, osteolytic bone disease and periodontal disease. Types of osteoporosis include primary osteoporosis, secondary osteoporosis, post-menopausal osteoporosis, male osteoporosis and steroid induced osteoporosis. Bone remodeling disorders includes metabolic bone diseases which are characterized by disturbances in the organic matrix, bone mineralization, bone remodeling, endocrine, nutritional and other factors which regulate skeletal and mineral homeostasis. Such disorders may be hereditary or acquired and generally are systemic, affecting the entire skeletal system.

Certain factors are well known in the art, which may be used to identify those at risk of developing a bone deficit due to bone remodeling disorders like osteoporosis. Important factors include low bone mass, family history, life style (e.g., diet, exercise), estrogen or androgen deficiency, negative calcium balance and taking drugs with a side effect of bone loss (e.g., cortisone-like drugs). Postmenopausal women are particularly at risk of developing osteoporosis. Additional risk factors for bone loss include advanced age, family history of bone disease (e.g., osteoporosis) and early symptoms of bone diseases including osteoporosis, Paget's disease, osteoarthritis, rheumatoid arthritis, achondroplasia, osteochondritis, hyperparathyroidism, osteogenesis imperfecta, congenital hypophosphatasia, fibromatous lesions, fibrous displasia, multiple myeloma, abnormal bone turnover, osteolytic bone disease and periodontal disease. In one embodiment of the invention, the risk factors do not include hyperparathyroidism. In another embodiment of the invention, the risk factors do not include hyperphosphatemia, alone or in combination with hyperparathyroidism.

Types of bone that can be treated by the method of the present invention include trabecular bone and cortical bone. Specific bones that can be treated by the present invention include the clavicle, scapula, humerus, ulna, radius, ilium, sacrum, vertebrae, hip bone, femur, fibula and tibia.

The invention also provides a method for enhancing bone formation in a mammal having a bone deficit that does not result from a bone remodeling disorder. These bone deficits can result from, for example, a bone fracture, bone trauma, or a condition associated with post-traumatic bone surgery, post-prosthetic joint surgery, post-plastic bone surgery, post-dental surgery, bone chemotherapy treatment or bone radiotherapy treatment. Fractures include all types of microscopic and macroscopic fractures. Examples of fractures includes avulsion fracture, comminuted fracture, transverse fracture, oblique fracture, spiral fracture, segmental fracture, displaced fracture, impacted fracture, greenstick fracture, torus fracture, fatigue fracture, intraarticular fracture (epiphyseal fracture), closed fracture (simple fracture), open fracture (compound fracture) and occult fracture. In one embodiment of the invention, the bone deficits listed above are not associated with hyperphosphatemia, alone or in combination with hyperparathyroidism.

The effectiveness of the above-described methods can be assessed by a variety of methods. Biochemical markers provide a first method of analyzing effectiveness. Treatment of osteoporosis typically involves an increase in osteoblast function and/or a decrease in osteoclast function. An increase in osteoblast function is typically characterized by an increase in blood levels of osteocalcin and/or bone-specific alkaline phosphatase (BSAP). An increase in osteoclast function can be detected by an elevation in levels of C-telopeptides, N-telopeptides, hydroxyproline (OHP) and/or deoxypyridinoline (DPD) excreted in the urine. A change in bone mineral density can also be measured using a method such as electron beam (computerized) tomography (EBT or EBCT) or other densitometric methods.

Aliphatic amine polymers can also be co-administered with one or more additional pharmaceutical agents. Suitable pharmaceutical agents include lanthanum(III) compounds such as lanthanum chloride, lanthanum carbonate, lanthanum salts (e.g., lanthanum carbonate, lanthanum carbonate hydrate, lanthanum chloride), chelates or derivatives thereof, lanthanum resins and lanthanum absorbants. Other suitable pharmaceutical agents include natural or synthetic hormones, such as estrogens, androgens, calcitonin, prostaglandins and parathormone; growth factors, such as platelet-derived growth factor, insulin-like growth factor, transforming growth factor, epidermal growth factor, connective tissue growth factor and fibroblast growth factor; vitamins, particularly vitamin D and its analogues (e.g., paricalcitol); mineral-forming substances, such as calcium, aluminum, strontium and fluoride; statin drugs, including pravastatin, fluvastatin, simvastatin, lovastatin and atorvastatin; agonists or antagonists of receptors on the surface of osteoblasts and osteoclasts, including parathormone receptors, estrogen receptors and prostaglandin receptors; bisphosphonates and anabolic bone agents.

The invention is illustrated by the following examples which are not intended to be limiting in any way.

EXEMPLIFICATION

EXAMPLE 1

Clinical Testing

Patient Studies

Protocols 1–7 for use of RenaGel® (Geltex Pharmaceuticals, Inc., Waltham, Mass.) in each of the haemodialysis patient studies are provided in the following references, respectively, the teachings of which are incorporated herein by reference in their entireties.

Protocol 1:
Chertow, G. M., Burke, S. K., Lazarus, J. M., Stenzel, K. H., Wombolt, D., Goldberg, D., Bonventre, J. V., and Slatopolsky, E., "Poly(allylamine hydrochloride) (RenaGel®): a noncalcemic phosphate binder for the treatment of hyperphosphatemia in chronic renal failure," *Am. J Kid. Dis.* 29: 66–71 (1997).

Protocol 2:
Goldberg, D. I., Dillon, M. A., Slatopolsky, E. A., Garrett ,B., Gray, J. R., Marbury, T., Weinberg, M., Wombolt, D., and Burke, S. K., "Effect of RenaGel, a non-absorbed, calcium-and aluminum-free phosphate binder, on serum phosphorus, calcium, and intact parathyroid hormone in end-stage renal disease patients," *Nephrol. Dial. Transplant.* 13: 2303–2310 (1998).

Protocol 3:
Chertow, G. M., Dillon, M., Burke, S. K., Steg, M., Bleyer, A. J., Garrett, B. N., Domoto, D. T., Wilkes, B. M., Wombolt, D. G., and Slatopolsky, E., "A randomized trial of sevelamer hydrochloride (RenaGel®) with and without supplemental calcium. Strategies for the control of hyperphosphatemia in hemodialysis patients," *Clin. Nephrol.* 51: 18–26 (1999).

Protocol 4:
Bleyer, A. J., Burke, S. K., Dillon, M., Garrett, B., Kant, K. S., Lynch, D., Raman, S. N., Shoenfeld, P., Teitelbaum, I., Zieg, S., and Slatopolsky, E., "A comparison of the calcium-free phosphate binder sevelamer hydrochloride with calcium acetate in the treatment of hyperphosphatemia in hemodialysis patients," *Am. J Kid. Dis.* 33: 694–701 (1999).

Protocol 5:

Slatopolsky, E., Burke, S. K., Dillon, M. A., and the RenaGel Study Group, "RenaGel®, a nonabsorbed calcium- and aluminum-free phosphate binder, lowers serum phosphorus and parathyroid hormone," *Kidney Int.* 55: 299–307 (1999).

Protocol 6:

Chertow, G. M., Burke, S. K., Dillon, M. A., and Slatopolsky, E., for the RenaGel Study Group, "Long-term effects of sevelamer hydrochloride on the calcium x phosphorus product and lipid profile of haemodialysis patients," *Nephol. Dial. Transplant.* 14: 2907–2914 (1999).

Protocol 7:

Chertow, G. M., Burke, S. K., Raggi, P., for the Treat to Goal Working Group, "Sevelamer attenuates the progression of coronary and aortic calcification in hemodialysis patients," *Kidney Int.* 62: 245–252 (2002).

Results

Biochemical Marker Studies

Osteocalcin and BSAP are measures of osteoblast function and are indicative of bone formation. Osteocalcin and BSAP are displayed during the chronic phase by screening intact parathyroid hormone (iPTH) levels. There were statistically significantly greater mean increases for the Renagel® group in osteocalcin (Renagel®, 58.86 ng/mL; calcium, 15.80 ng/ml; p=0.0003) and BSAP (Renagel® 20.39 U/L; calcium, 6.81 U/L; p<0.0001) at the end of the chronic phase of the study. There were no statistically significant differences between treatment groups in the mean change from Day 0 to Week 52 in c-telopeptides, a collagen fragment which indicates osteoclast function and bone resorption.

Bone Density Studies

The study was a 52 week, randomized, open label, multicenter, parallel study designed to assess the effects of sevelamer compared to calcium acetate/carbonate in enabling hemodialysis patients to reach therapeutic goals of phosphorus <5 mg/dL, calcium <10.5 mg/dL and iPTH in the range of 150–300 pg/mL. Patients also underwent Electron Beam Tomography (EBT) scans at Day 0 and Weeks 26 and 52. These scans were used to assess changes in cardiovascular calcification over time. A total of 202 patients who were on hemodialysis and taking one or more phosphate binders were randomized in a 1:1 design to receive either Renagel® or calcium acetate (United States)/carbonate (Europe), stratified by the presence or absence of diabetes.

Prior to the completion and analysis of this protocol, the study was extended for an additional two years. During this extension study, patients would remain on the phosphate binder to which they were originally randomized, sevelamer or calcium acetate/carbonate, and EBT scans would be performed at Month 24 and Month 36, to assess long-term changes in cardiovascular calcification. Forty-five patients in the US and 72 patients in the EU were eligible and consented to participate in the Extension study.

Approximately 12 months into the Extension study, the analysis of the initial study was completed. The cardiovascular calcification data revealed a significant difference between treatment groups. Overall, patients in the sevelamer group had a median change of 0.00 in coronary artery calcification by Agatston score from Week 0 to 52, while patients in the calcium group had a median increase of 36.55. This difference was statistically significant (p=0.0398). Similarly, patients in the Renagel group had a median change of 0.00 in aortic calcification by Agatston score from Week 0 to 52, while patients in the calcium group had a median increase of 75.05. This difference was statistically significant (p=0.0104). When analyzed by percent change and weekly change, the results were consistently in favor of the sevelamer group. Complete results are described in the article referenced as Protocol 7 (Chertow, 2002).

Having met the endpoints of the original study, the Extension study was prematurely discontinued. Only 77 Extension study patients opted to have a final EBT scan performed.

The study's EBT Core Lab evaluated the EBT images of patients who had both a baseline and 24 month scan to assess changes over time in trabecular and cortical bone density. Specifically, thoracic spine bone density was assessed by computerized tomography densitometry (density expressed as Hounsfield units). Trabecular bone density was measured in the core of the lowest vertebral body completely captured by the scanning procedure, while cortical bone density was measured in the axial plate of the same vertebral body. Care was taken to evaluate exactly the same vertebral level in consecutive scans in the same patient. No significant differences in demographics, baseline bone density or vascular calcification scores were observed between the sevelamer and calcium groups, with the exception of age, (sevelamer/Renagel group 53±12 yrs, calcium group 59±13 yrs, p=0.02). An analysis of covariance, however, demonstrated that the baseline age difference did not influence the final results.

The results are summarized in FIG. 1. During the two years, the sevelamer group had a significant increase in trabecular bone density and a non-significant increase in cortical density from baseline. In contrast, the calcium group experienced a significant reduction in trabecular bone density and a non-significant decrease in cortical bone density.

EXAMPLE 2

Upon finding that there were effects on bone in the patients studied in Example 1, an additional analysis was conducted in the larger group of patients from the original study who had a baseline and 12 month bone density scan.

Results

The study groups (calcium and sevelamer) were well balanced by randomization. At baseline, there were no significant differences between groups for any biochemical parameter measured except for slightly higher HDL cholesterol in the group randomized to calcium compared (calcium 50±17 mg/dL vs. sevelamer 44±15 mg/dL, p=0.04).

Following the 12 months of treatment, the levels a number of biochemical markers were assayed in the patient groups. Serum phosphorus and calcium-phosphorus product were not significantly different between treatment groups. The group treated with sevelamer had on average higher iPTH, 1–84 PTH, alkaline phosphatase, bone specific alkaline phosphatase, osteocalcin, and HDL cholesterol. The sevelamer group had lower calcium, 25-hydroxyvitamin D, total cholesterol, LDL cholesterol, apolipoprotein B, HDL cholesterol and total $CO_2$.

At baseline, cortical bone was significantly denser than trabecular bone, as expected, and there were no significant differences between the treatment groups for either cortical or trabecular bone.

Correlations between baseline bone density and baseline coronary artery and aortic calcification demonstrated significant negative correlations for trabecular bone for both coronary artery (r=−0.43, p<0.0001) and aorta (r=−0.18, p=0.05). Thus patients with low bone density were more likely to have vascular calcification.

Figure 3:
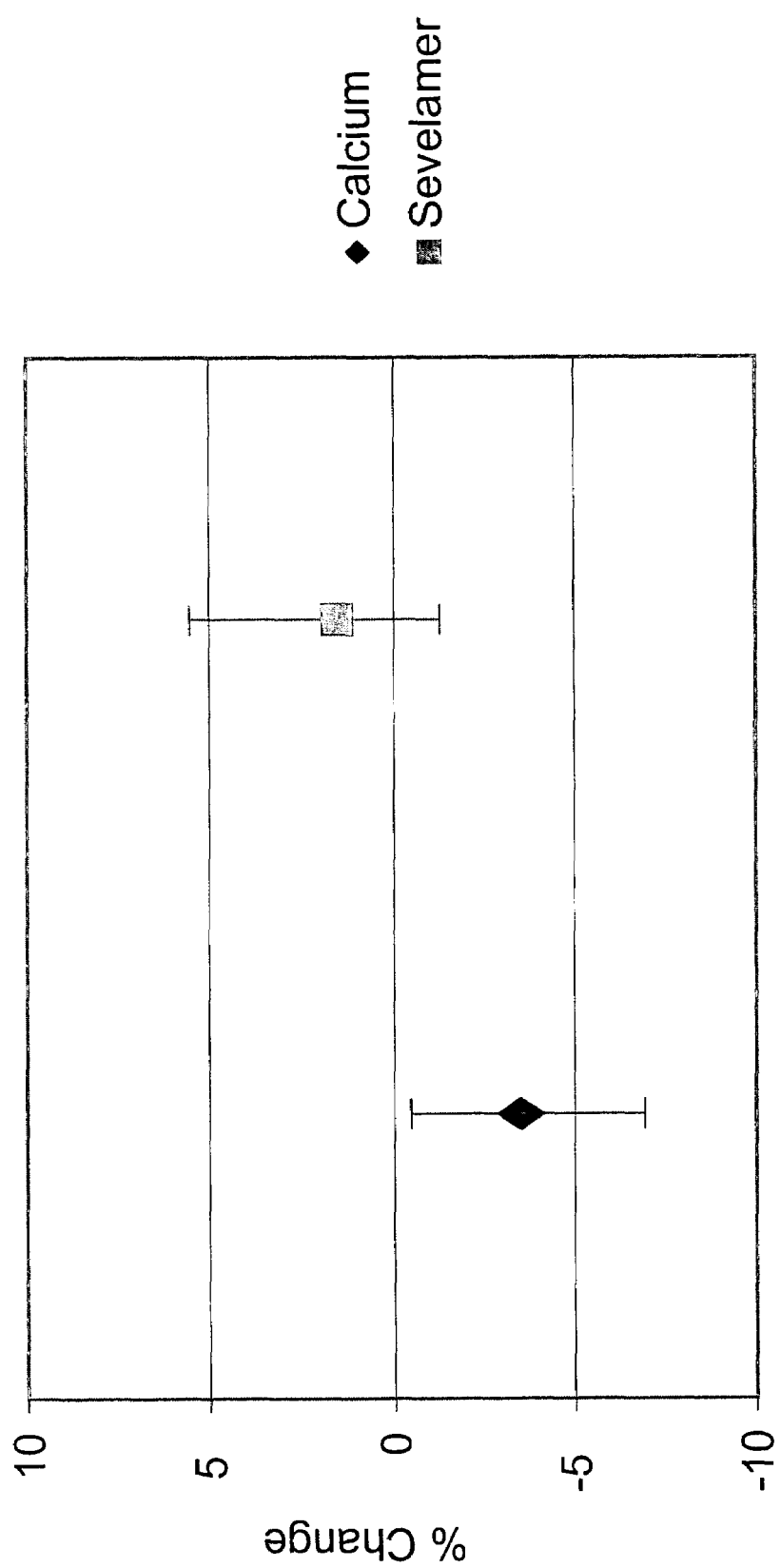
FIG. 3 shows the mean percent change in trabecular bone density over the one year period analyzed in Example 2. The bars indicate the 95% confidence interval.
Figure 4:
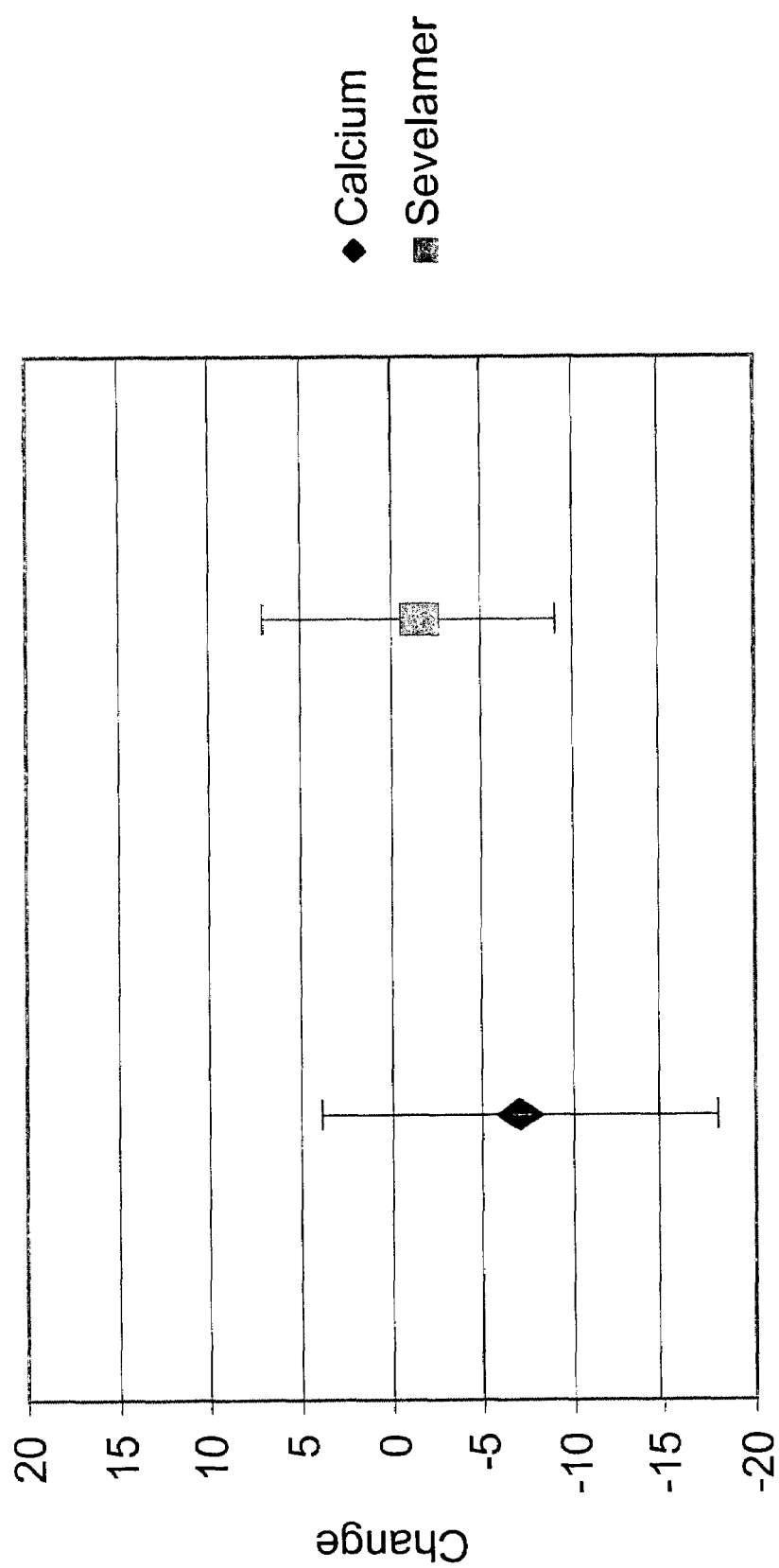
FIG. 4 shows the mean change in cortical bone density over the one year period analyzed in Example 2. The bars indicate the 95% confidence interval.
Figure 5:
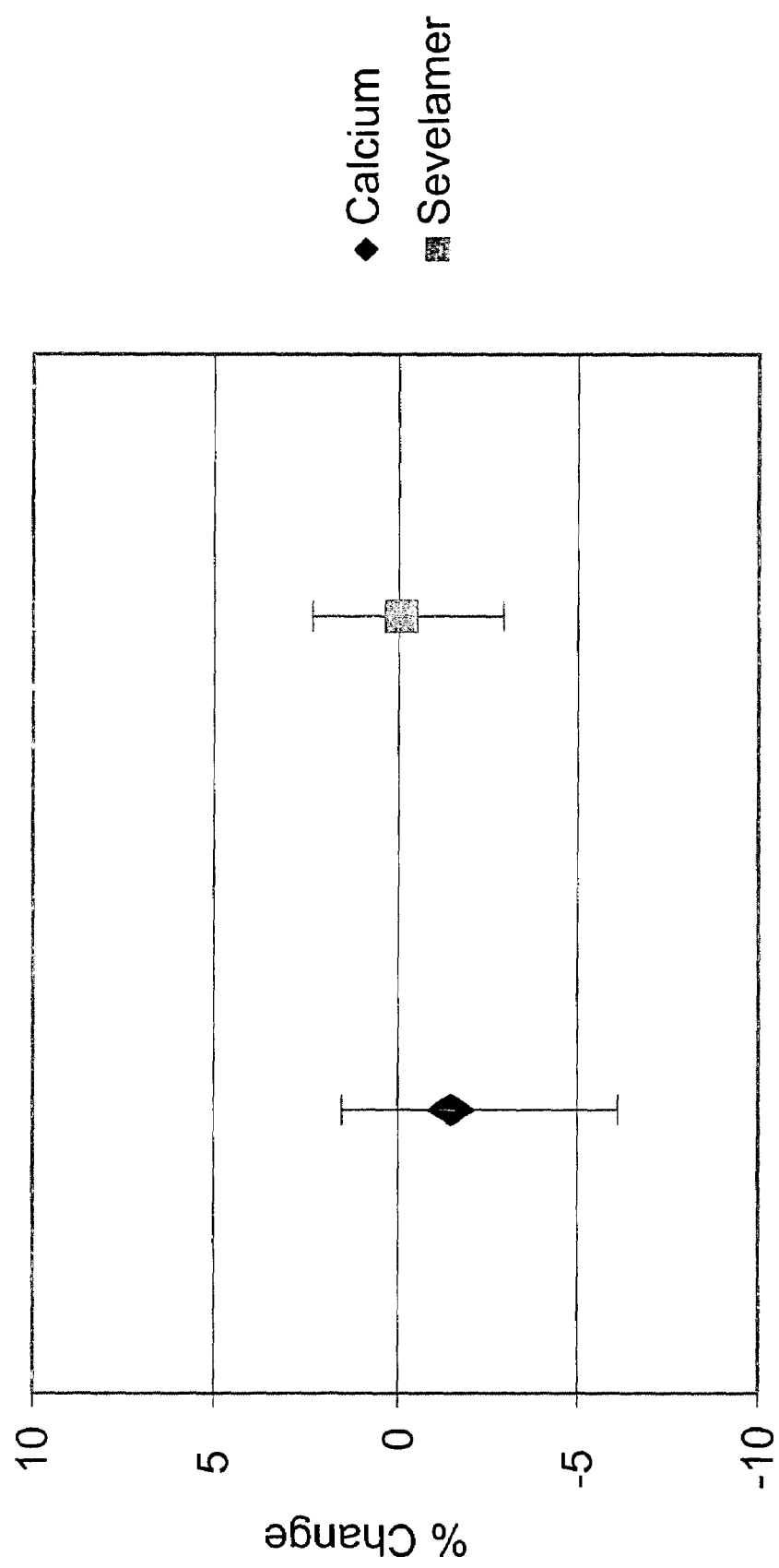
FIG. 5 shows the mean percent change in cortical bone density over the one year period analyzed in Example 2. The bars indicate the 95% confidence interval.

During the 12 month treatment period, the calcium group experienced a significant reduction in trabecular bone density (absolute change, p=0.002 1; percentage change, p=0.0009) and a trend to reduced cortical bone density when measured as absolute change (p=0.0565) or percentage change (p=0.0835): In contrast, the sevelamer treated group had no significant changes in either trabecular (absolute change, p=0.4456, percentage change, p=0.4930) or cortical (absolute change, p=0.4358, percentage change, p=0.4338) bone density. These data are illustrated in FIGS. 2–5.

It is believed that the reason significant bone growth is seen in the population studied over 24 months, but not in the population studied over 12 months, is due to the length of treatment and the speed at which new bone is generated. Bone growth continues over the full 24 month period, and apparently more than 12 months are required to observe a significant amount of bone growth in the patient group. There are no data that would indicate that differences among patient population (the 24 month group is a subset of the 12 month group) account for the significant results observed at 24 months.

A multivariate regression model using either change or percentage change in trabecular bone density as the dependent variable demonstrated a significant effect of treatment. There were no significant interactions of age, race, sex, or diabetes on treatment. Adjusting for differences in age, race, sex, and diabetes in a final model did not significantly impact the change of trabecular bone density in the two treatment groups.

A striking finding of the study was that calcium use over a period of 52 weeks was not associated with preservation of bone density. The results documented a clear loss of trabecular bone density and a strong trend to loss of cortical bone density (p=0.06) in the calcium group, which was not seen in the sevelamer treated group. The magnitude of trabecular bone density loss, a mean of −5%, is substantially greater than that observed in the general elderly non-renal failure population but consistent with the loss observed in dialysis patients measured by DEXA. This bone loss with calcium occurred despite significantly lower iPTH in the calcium treated group relative to the sevelamer treated group.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for promoting bone formation in a mammal in need thereof by administering to the mammal a therapeutically effective amount of at least one amine polymer with the proviso that said mammal is not suffering from hyperparathyroidism, hyperphosphatemia or osteitis fibrosa; wherein
   (a) said amine polymer comprises a repeat unit having a formula selected from the group consisting of:

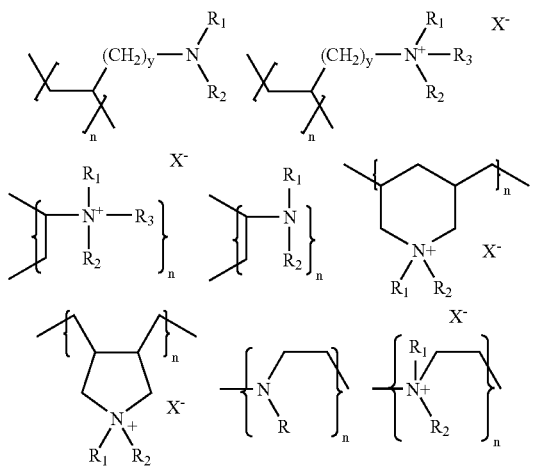

or a salt or a copolymer thereof, where n is a positive integer and y is an integer of one or more, each R, $R_1$, $R_2$ and $R_3$, independently, is H or a substituted or unsubstituted alkyl group, and $X^-$ is an exchangeable negatively charged counterion,
   (b) said amine polymer is cross-linked by means of a multifunctional cross-linking agent, and
   (c) said multifunctional cross-linking agent is present in an amount from about 0.5–25% by weight, based upon the combined weight of monomer and cross-linking agent.

2. The method of claim 1 wherein the multifunctional cross-linking agent is present in an amount from about 2.5–20% by weight, based upon the combined weight of monomer and cross-linking agent.

3. The method of claim 1 wherein said cross-linking agent comprises epichlorohydrin.

4. The method of claim 1 wherein the polymer is a homopolymer.

5. The method of claim 4 wherein the polymer is a polyallylamine.

6. The method of claim 4 wherein the polymer is a polydiallylamine.

7. The method of claim 4 wherein the polymer is a polyvinylamine.

8. The method of claim 1 wherein at least one of R, $R_1$, $R_2$, and $R_3$ in each formula is hydrogen.

9. The method of claim 1 wherein the polymer is administered with one or more meals.

10. The method of claim 1 wherein said amine polymer is a copolymer.

11. The method of claim 10 wherein said copolymer comprises non-amine containing monomers.

12. The method of claim 1 wherein said amine polymer is administered as a salt.

13. The method of claim 12 wherein said salt comprises chloride.

14. The method of claim 12 wherein said salt comprises carbonate.

15. The method of claim 1 wherein said therapeutically effective amount of said amine polymer is administered to said mammal in the form of a pharmaceutical composition comprising said amine polymer and a pharmaceutically acceptable carrier or diluent.

16. A method of treating a mammal suffering from osteoporosis by administering to the mammal a therapeutically effective amount of at least one amine polymer with the proviso that said mammal is not suffering from hyperparathyroidism, hyperphosphatemia or osteitis fibrosa; wherein
(a) said amine polymer comprises a repeat unit having a formula selected from the group consisting of:

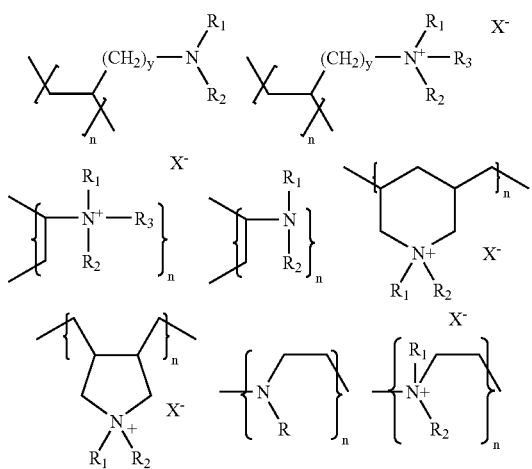

or a salt or a copolymer thereof, where n is a positive integer and y is an integer of one or more, each R, $R_1$, $R_2$ and $R_3$, independently, is H or a substituted or unsubstituted alkyl group, and $X^-$ is an exchangeable negatively charged counterion,
(b) said amine polymer is cross-linked by means of a multifunctional cross-linking agent, and
(c) said multifunctional cross-linking agent is present in an amount from about 0.5–25% by weight, based upon the combined weight of monomer and cross-linking agent.

17. The method of claim 16 wherein the multifunctional cross-linking agent is present in an amount from about 2.5–20% by weight, based upon the combined weight of monomer and cross-linking agent.

18. The method of claim 16 wherein said cross-linking agent comprises epichlorohydrin.

19. The method of claim 16 wherein the polymer is a homopolymer.

20. The method of claim 19 wherein the polymer is a polyallylamine.

21. The method of claim 19 wherein the polymer is a polydiallylamine.

22. The method of claim 19 wherein the polymer is a polyvinylamine.

23. The method of claim 16 wherein at least one of R, $R_1$, $R_2$, and $R_3$ in each formula is hydrogen.

24. The method of claim 16 wherein the polymer is administered with one or more meals.

25. The method of claim 16 wherein said amine polymer is a copolymer.

26. The method of claim 16 wherein said copolymer comprises non-amine containing monomers.

27. The method of claim 16 wherein said amine polymer is administered as a salt.

28. The method of claim 27 wherein said salt comprises chloride.

29. The method of claim 27 wherein said salt comprises carbonate.

30. The method of claim 16 wherein said therapeutically effective amount of said amine polymer is administered to said mammal in the form of a pharmaceutical composition comprising said amine polymer and a pharmaceutically acceptable carrier or diluent.

* * * * *